United States Patent [19]

Korn

[11] 4,023,642
[45] May 17, 1977

[54] SOUNDPROOF EARCOVERS

[75] Inventor: Bernard Korn, Brooklyn, N.Y.

[73] Assignee: The Raymond Lee Organization, Inc., New York, N.Y.

[22] Filed: June 25, 1975

[21] Appl. No.: 590,094

[52] U.S. Cl. .................. 181/33 R; 2/209; 128/152; 181/129
[51] Int. Cl.² .................. A01F 11/02; G10K 11/04
[58] Field of Search .................. 181/129–131, 181/137, 33 R; 128/151, 152; 2/209, 6

[56] References Cited

UNITED STATES PATENTS

| 437,602 | 9/1890 | Kaiser | 128/152 |
| 997,673 | 7/1911 | Hegge | 128/152 |
| 2,215,198 | 9/1940 | Silbert | 128/152 |
| 2,345,842 | 4/1944 | Valentine | 128/152 |
| 2,570,675 | 10/1951 | Morris | 128/151 |
| 2,802,214 | 8/1957 | Hanks | 128/152 |
| 2,883,671 | 4/1959 | Hornickel | 128/151 |
| 3,016,054 | 1/1962 | Rosenblatt | 128/152 |
| 3,321,041 | 5/1967 | Bowen, Jr. | 181/131 |

Primary Examiner—Stephen J. Tomsky
Attorney, Agent, or Firm—Stephen Wyden

[57] ABSTRACT

A pair of shells filled with foam and ear plugs to cover the ears and exclude all sound.

2 Claims, 2 Drawing Figures

SOUNDPROOF EARCOVERS

I have invented a new and novel soundproof earcover which will prevent a user from hearing any sound thus permitting the user to concentrate in peace under adverse conditions. My invention can be understood in view of the accompanying figures.

In FIG. 1, a user 10 has a set of earcovers 20 mounted on his head over his ears.

Figure 1:
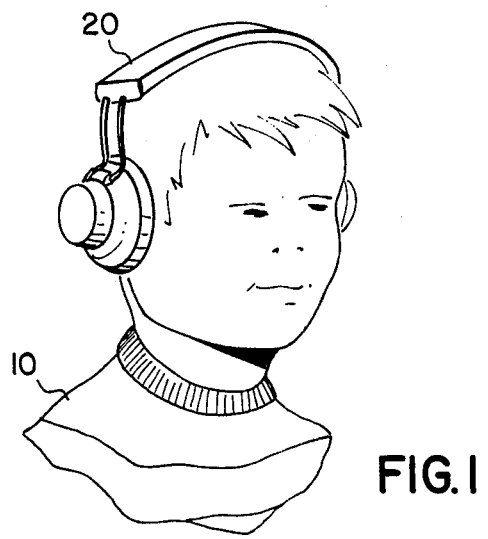
FIG. 1 shows a user with the soundproof covers.
Figure 2:
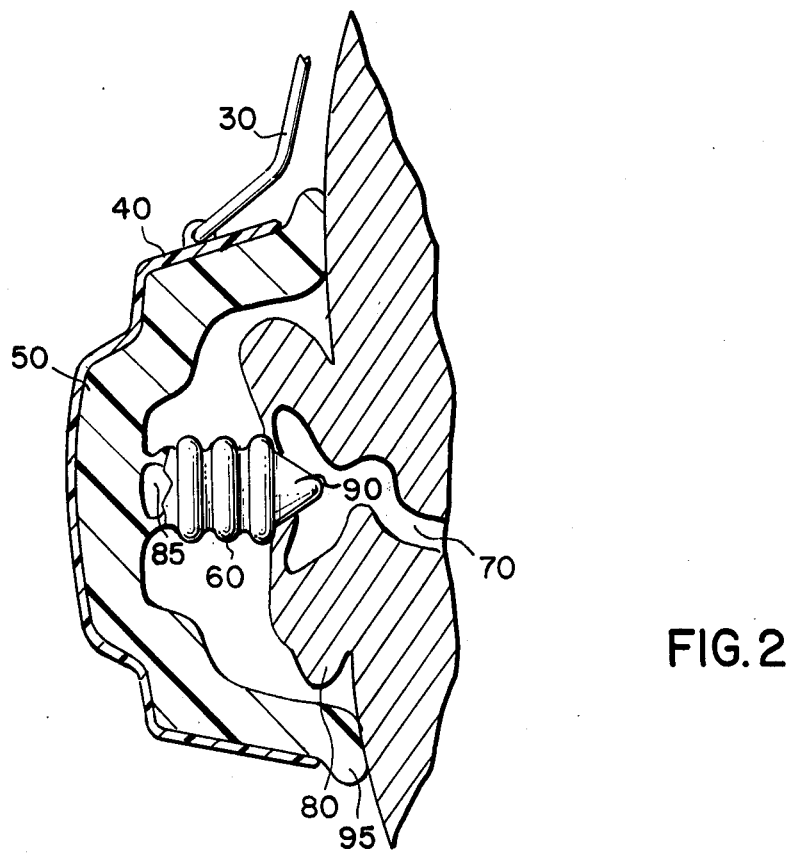
FIG. 2 shows the details of the earcover in cross section.

In FIG. 2, the earcover comprises a strap 30 connecting the individual earcovers attached to an outershell 40 to maintain the shape of the earcover and form a cavity against the user's head, a flexible foam insulation layer 50 under the shell 40, an inner earplug 60 mounted on the foam 50 to seal the ear canal 70 and thereby cut out direct sounds from reaching the ear 80 as the foam 50 prevents indirect sounds from reaching the ear.

It is to be noted that the inner ear plug 60 forms a hollow core 85 and flexible ridges and a tapered conical tip 90. The plug 60 is an extension of the foam 50 and is adjustable to the user's ear 80. The foam 50 is adjustable at the edges 95 to the shape of the head of the user 10 so as to enclose the ear 80.

Having described a preferred embodiment of my invention, it is understood that various changes can be made without departing from the spirit of my invention, and, I desire to cover by the appended claims all such modifications as fall within the true spirit and scope of my invention.

What I claim and seek to secure by Letters Patent is:

1. A soundproof earcover, comprising:
    an outer shell forming a cavity to cover an ear, when in contact with a head,
    a flexible foam insulation deposited in the outer shell,
    an ear plug mounted on the foam, thereby forming a seal for an ear canal of the user,
    a strap attached to the ear cover and mounted over the head of the user,
    a second ear cover attached to the distal end of the strap, thereby forming a set of earcovers, whereby all sound may be prevented from reaching the user, and
    the plug forming a hollow central core and forming flexible ridges.

2. The ear cover of claim 1, wherein the foam extends beyond the shell to releaseably engage a portion of a head of a head of the user surrounding each of the ears.